United States Patent
Ogura et al.

(10) Patent No.: US 6,788,415 B2
(45) Date of Patent: Sep. 7, 2004

(54) TURNTABLE MEASURING APPARATUS UTILIZING ATTENUATED TOTAL REFLECTION

(75) Inventors: Nobuhiko Ogura, Kaisei-machi (JP); Nobufumi Mori, Kaisei-machi (JP)

(73) Assignee: Fuji Photo Film Co., Ltd., Kanagawa-Ken (JP)

(*) Notice: Subject to any disclaimer, the term of this patent is extended or adjusted under 35 U.S.C. 154(b) by 97 days.

(21) Appl. No.: 10/113,928

(22) Filed: Apr. 2, 2002

(65) Prior Publication Data

US 2002/0180975 A1 Dec. 5, 2002

(30) Foreign Application Priority Data

Apr. 2, 2001 (JP) .................................. 2001-103461
Mar. 7, 2002 (JP) .................................. 2002-062049

(51) Int. Cl.[7] .............................................. G01N 21/55
(52) U.S. Cl. ............................................ 356/445; 422/64
(58) Field of Search ............................ 356/445; 422/64

(56) References Cited

U.S. PATENT DOCUMENTS 4,781,891 A * 11/1988 Galle et al. .................... 422/64
5,100,622 A * 3/1992 Mimura et al. ................ 422/67
5,470,757 A * 11/1995 Gagnon et al. ............. 422/82.08
5,730,938 A * 3/1998 Carbonari et al. .............. 422/64
6,289,144 B1 * 9/2001 Neuschafer et al. ....... 422/82.11

FOREIGN PATENT DOCUMENTS

JP        6-167443        6/1994
JP        2001-49681      2/2001

OTHER PUBLICATIONS

Takayuki Okamoto, "Spectral Researches" vol. 47, No. 1, 1998, pp. 21–23 and 26–27.
U.S.S.N. 09/959,645, Q66884, filed Nov. 2, 2001.

* cited by examiner

Primary Examiner—F. L. Evans
Assistant Examiner—Kara Geisel
(74) Attorney, Agent, or Firm—Sughrue Mion, PLLC (57) ABSTRACT

A measuring apparatus includes a turntable and drive means. The turntable is used for supporting n measuring units at intervals of a predetermined angle with respect to a rotation axis thereof. The drive means is used for rotating the turntable intermittently at intervals of an angle equal to m times the predetermined angle (m is an integer). When the turntable is stopped, k kinds of processes are respectively performed on the measuring units situated at different positions on the turntable. The above-mentioned k is $2 \leq k \leq n$, and the above-mentioned m is either 1, a number that is neither the common divisor of 1 and n nor the common multiple, or a sum of 1 and the common multiple of n.

3 Claims, 6 Drawing Sheets

TURNTABLE MEASURING APPARATUS UTILIZING ATTENUATED TOTAL REFLECTION

BACKGROUND OF THE INVENTION

1. Field of the Invention

The present invention relates to a measuring apparatus utilizing attenuated total reflection (ATR), such as a surface plasmon resonance measuring apparatus for quantitatively analyzing a substance in a sample by utilizing the excitation of surface plasmon, and more particularly to a measuring apparatus, utilizing ATR, which can measure a large number of samples in a short time. The present invention also relates to a measuring apparatus that can measure a large number of samples in a short time.

2. Description of the Related Art

In metals, if free electrons are caused to vibrate in a group, a compression wave called a plasma wave will be generated. The compression wave, generated in the metal surface and quantized, is called surface plasmon.

There have hitherto been proposed various kinds of surface plasmon resonance measuring apparatuses for quantitatively analyzing a substance in a sample by taking advantage of a phenomenon that surface plasmon is excited by a light wave. Among such apparatuses, one employing a system called the "Kretschmann configuration" is particularly well known (e.g., see Japanese Unexamined Patent Publication No. 6(1994) -167443).

The surface plasmon resonance measuring apparatus employing the "Kretschmann configuration" is equipped with a dielectric block formed, for example, into the shape of a prism; a metal film, formed on one surface of the dielectric block, for placing a sample thereon; and a light source for emitting a light beam. The measuring apparatus is further equipped with an optical system for making the light beam enter the dielectric block so that a condition for total internal reflection (TIR) is satisfied at the interface between the dielectric block and the metal film and that various angles of incidence, including a surface plasmon resonance condition, are obtained; and photodetection means for measuring the intensity of the light beam totally reflected at the interface, and detecting surface plasmon resonance.

To obtain various angles of incidence in the aforementioned manner, a relatively thin light beam can be deflected so that it strikes the above-mentioned interface at different angles of incidence, or a relatively thick beam can be convergently emitted so that the components thereof strike the interface at various angles of incidence. In the former, the light beam whose reflection angle varies with the deflection thereof can be detected by a small photodetector that is moved in synchronization with the light beam deflection, or by an area sensor extending along a direction where the reflection angle varies. In the latter, on the other hand, the light beams reflected at various angles can be detected by an area sensor extending in a direction where all the reflected light beams are received.

In the surface plasmon resonance measuring apparatus mentioned above, an evanescent wave having electric field distribution is generated in a sample in contact with the metal film, if a light beam strikes the metal film at a specific incidence angle $\theta_{sp}$ greater than a critical incidence angle at which total internal reflection (TIR) takes place. The generated evanescent wave excites surface plasmon at the interface between the metal film and the sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light satisfying TIR at the interface between the dielectric block and the metal film drops sharply. This sharp intensity drop is generally detected as a dark line by the above-mentioned photodetection means.

Note that the above-mentioned resonance occurs only when an incident light beam is a p-polarized light beam. Therefore, in order to make the resonance occur, it is necessary that a light beam be p-polarized before it strikes the interface.

If the wave number of the surface plasmon is found from the specific incidence angle $\theta_{sp}$ at which attenuated total reflection (ATR) takes place, the dielectric constant of a sample to be analyzed can be calculated by the following Equation:

$$K_{sp}(\omega)=(\omega/c)\{\epsilon_m(\omega)\epsilon_s\}^{1/2}/\{\epsilon_m(\omega)+\epsilon_s\}^{1/2}$$

where $K_{sp}$ represents the wave number of the surface plasmon, $\omega$ represents the angular frequency of the surface plasmon, c represents the speed of light in vacuum, and $\epsilon_m$ and $\epsilon_s$ represent the dielectric constants of the metal and the sample, respectively.

If the dielectric constant $\epsilon_s$ of a sample is found, the density of a specific substance in the sample is found based on a predetermined calibration curve, etc. As a result, the specific substance in the sample can be quantitatively analyzed by finding the specific incidence angle $\theta_{sp}$ at which the intensity of the reflected light at the interface drops sharply.

As a similar sensor making use of ATR, there is known a leaky mode sensor (e.g., see "Spectral Researches," Vol. 47, No. 1 (1998), pp. 21 to 23 and pp. 26 to 27). This leaky mode sensor is equipped with a dielectric block formed, for example, into the shape of a prism; a cladding layer formed on one surface of the dielectric block; and an optical waveguide layer, formed on the cladding layer, for placing a sample thereon. The leaky mode sensor is further equipped with a light source for emitting a light beam; an optical system for making the light beam enter the dielectric block at various angles of incidence so that a condition for total internal reflection (TIR) is satisfied at the interface between the dielectric block and the cladding layer and so that ATR occurs by a waveguide mode excited in the optical waveguide layer; and photodetection means for measuring the intensity of the light beam totally reflected at the interface between the dielectric block and the cladding layer, and detecting the excited state of the waveguide mode, that is, ATR.

In the leaky mode sensor mentioned above, if a light beam strikes the cladding layer through the dielectric block at incidence angles greater than a critical incidence angle at which TIR takes place, the light beam is transmitted through the cladding layer and then only light with a specific wave number, incident at a specific incidence angle, propagates through the optical waveguide layer in a waveguide mode. If the waveguide mode is excited in this manner, the greater part of the incident light is confined within the optical waveguide layer, and consequently, ATR occurs in which the intensity of light totally reflected at the above-mentioned interface drops sharply. Since the wave number of the light propagating through the optical waveguide layer depends on the refractive index of a sample on the optical waveguide layer, both the refractive index of the sample and the properties of the sample related to the refractive index thereof can be analyzed by finding the above-mentioned specific incidence angle $\theta_{sp}$ at which ATR takes place.

In the field of pharmaceutical manufacture and the like, the above-mentioned surface plasmon resonance measuring apparatus and leaky mode measuring apparatus are sometimes used in a random screening method for detecting a specific substance that bonds with a predetermined sensing substance. In this case, the sensing substance is placed on the aforementioned thin film layer (i.e., the metal film in the case of the surface plasmon resonance measuring apparatus, or the cladding layer and optical waveguide layer in the case of the leaky mode sensor). Then, a liquid sample containing a target substance is dropped into the sensing substance, and each time a predetermined time elapses, the aforementioned specific incidence angle $\theta_{sp}$ is measured.

If the target substance in the liquid sample bonds with the sensing substance, the refractive index of the sensing substance varies with the lapse of time by the bond therebetween. Therefore, every time a predetermined time elapses, the specific incidence angle $\theta_{sp}$ is measured. Based on the measured value, the bond between the target substance and the sensing substance is measured. Next, based on the result, it can be judged whether or not the target substance is a specific substance that bonds with the sensing substance. An example of combination of the specific substance and the sensing substance is an antigen and an antibody. As an example of a measurement of such combination, there is a measurement of the bond between a human IgG (immunoglobulin G) antibody in a target substance and a rabbit antihuman IgG antibody (sensing substance).

Note that the specific incidence angle $\theta_{sp}$ itself does not always need to be detected to measure the bond between the target substance and the sensing substance. For example, a liquid sample is added to the sensing substance; then a change in the specific incidence angle $\theta_{sp}$ thereafter is measured; and based on the angle change, the bond can be measured.

However, a measuring apparatus, such as the aforementioned surface plasmon resonance sensor and leaky mode sensor, has the disadvantage that when measuring a plurality of samples, the measurement is extremely time-consuming. Particularly, in the case in which a single sample is measured several times at predetermined temporal intervals in order to detect a change in the properties of the sample due to an antigen-antibody reaction, a chemical reaction, etc., a new sample cannot be measured unless the measurement of the single sample is finished, and consequently, it takes too much time to measure all samples.

In view of the circumstances mentioned above, there has been proposed a measuring apparatus, utilizing ATR, which can measure a large number of samples in a short time (see Japanese Patent Application No. 2001-49681). In this measuring apparatus utilizing ATR, the aforementioned dielectric block, the thin film layer formed on one surface of the dielectric block (the metal film in the case of the surface plasmon resonance measuring apparatus, or the cladding layer and the optical waveguide layer in the case of the leaky mode measuring apparatus), and the sample holding mechanism for holding a sample on the thin film layer, are integrated into a measuring unit. The measuring apparatus is provided with a turntable and drive means for driving the turntable intermittently. The turntable is used for supporting a plurality of measuring units at predetermined intervals with respect to a rotation axis thereof. The measuring units on the turntable are serially stopped at a position where the aforementioned light beam is irradiated.

In the above-mentioned measuring apparatus utilizing ATR, when the irradiation of the light beam and the intensity detection of the totally reflected light are being performed on the measuring unit held at a predetermined position on the turntable being stopped, another process is simultaneously performed on another measuring unit held at another position. In this manner, the efficiency of the measuring operation is enhanced. Examples of the other process are the process of supplying a sample to a measuring unit, the process of pouring oil into the measuring unit with the sample to prevent evaporation of the sample, the process of removing the measuring unit for which measurements were made, from the turntable, the process of supplying a new measuring unit to the turntable, and so on.

In the above-mentioned measuring apparatus utilizing ATR, the samples held in the sample holding mechanisms of a plurality of measuring units can be serially measured by rotation of the turntable. Thus, according to the measuring apparatus, a large number of samples can be measured in a short time.

In addition, in the case where measuring units with a sample to be analyzed are generally employed in a measuring apparatus other than a measuring apparatus employing ATR, the measuring units are supported by a turntable, and each time the turntable is stopped, various processes are performed on the measuring unit. In this manner, as with the aforementioned case, the time required for measurements can be shortened. Such processes, in addition to the aforementioned processes, include the process of adding a reagent which reacts with a target substance and the process of agitating a sample, and, in a blood analyzer, etc., include the process of measuring the absorbance of a reagent that has reacted with a sample (such as blood, etc.) and the process of detecting the wavelength and intensity of fluorescent light emitted from the aforementioned reagent. The items to be inspected by the measurement include an enzyme related item, a nitrogen contained component, lipid, an electrolyte, sugar metabolism inspection, vital pigment inspection, kidney function inspection (e.g., detection of α1 micro-globulin in serum and urine, β2 micro-globulin in urine, albumin in urine, Tf in urine, IgG in urine, etc.), plasma protein inspection (e.g., detection of IgG, IgA, IgM, IgD, C3, C4, transferrin, etc.), tumor marker inspection (e.g., detection of BFP, β2 micro-globulin in blood, IAP, etc.), etc.

SUMMARY OF THE INVENTION

The present invention has been made in view of the circumstances mentioned above. Accordingly, it is the primary object of the present invention to provide a measuring apparatus, such as a measuring apparatus utilizing ATR, which is capable of efficiently performing processes on measuring units situated at predetermined positions on a turntable.

To achieve this end and in accordance with the present invention, there is provided a first measuring apparatus comprising:

n measuring units;

a turntable for supporting the n measuring units at intervals of a predetermined angle with respect to a rotation axis thereof; and drive means for rotating the turntable intermittently at intervals of an angle equal to m times the predetermined angle (m is an integer);

wherein, when the turntable is stopped, k kinds of processes are respectively performed on the measuring units situated at different positions on the turntable;

and wherein the k is $2 \leq k \leq n$ and the m is either 1, a number that is neither the common divisor of the n nor the common multiple, or a sum of 1 and the common multiple of the n.

In accordance with the present invention, there is provided a second measuring apparatus utilizing attenuated total reflection, comprising:

n measuring units comprising
  a dielectric block, a thin film layer formed on one surface of the dielectric block, and a sample holding mechanism for holding a sample on the thin film layer;
a turntable for supporting the n measuring units at intervals of a predetermined angle with respect to a rotation axis thereof;
drive means for rotating the turntable intermittently at intervals of an angle equal to m times the predetermined angle (m is an integer);
a light source for emitting a light beam;
an optical system for making the light beam enter the dielectric block of the measuring unit, situated at a predetermined position when the turntable is stopped, at various angles of incidence so that a condition for total internal reflection is satisfied at an interface between the dielectric block and the metal film; and
photodetection means for measuring intensity of the light beam totally reflected at the interface to detect the attenuated total reflection;
wherein, when the turntable is stopped, k kinds of processes, including irradiation of the light beam and the detection of the intensity, are respectively performed on the measuring units situated at different positions on the turntable;
and wherein the k is $2 > k \leq n$ and the m is either 1, a number that is neither the common divisor of the n nor the common multiple, or a sum of 1 and the common multiple of the n.

In accordance with the present invention, there is provided a third measuring apparatus utilizing attenuated total reflection, comprising:

n measuring units comprising
  a dielectric block, a thin film layer, which comprises a metal film, formed on one surface of the dielectric block, and a sample holding mechanism for holding a sample on the thin film layer;
a turntable for supporting the n measuring units at intervals of a predetermined angle with respect to a rotation axis thereof;
drive means for rotating the turntable intermittently at intervals of an angle equal to m times the predetermined angle (m is an integer);
a light source for emitting a light beam;
an optical system for making the light beam enter the dielectric block of the measuring unit, situated at a predetermined position when the turntable is stopped, at various angles of incidence so that a condition for total internal reflection is satisfied at an interface between the dielectric block and the metal film; and
photodetection means for measuring intensity of the light beam totally reflected at the interface to detect the attenuated total reflection due to surface plasmon resonance;
wherein, when the turntable is stopped, k kinds of processes, including irradiation of the light beam and the detection of the intensity, are respectively performed on the measuring units situated at different positions on the turntable;
and wherein the k is $2 \leq k \leq n$ and the m is either 1, a number that is neither the common divisor of the n nor the common multiple, or a sum of 1 and the common multiple of the n.

In accordance with the present invention, there is provided a fourth measuring apparatus utilizing attenuated total reflection, comprising:

n measuring units comprising
  a dielectric block, a thin film layer, which comprises a cladding layer and an optical waveguide layer formed on the cladding layer, formed on one surface of the dielectric block, and a sample holding mechanism for holding a sample on the thin film layer;
a turntable for supporting the n measuring units at intervals of a predetermined angle with respect to a rotation axis thereof;
drive means for rotating the turntable intermittently at intervals of an angle equal to m times the predetermined angle (m is an integer);
a light source for emitting a light beam;
an optical system for making the light beam enter the dielectric block of the measuring unit, situated at a predetermined position when the turntable is stopped, at various angles of incidence so that a condition for total internal reflection is satisfied at an interface between the dielectric block and the cladding layer; and
photodetection means for measuring intensity of the light beam totally reflected at the interface to detect the attenuated total reflection due to a waveguide mode excited at the optical waveguide layer;
wherein, when the turntable is stopped, k kinds of processes, including irradiation of the light beam and the detection of the intensity, are respectively performed on the measuring units situated at different positions on the turntable;
and wherein the k is $2 \leq k \leq n$ and the m is either 1, a number that is neither the common divisor of the n nor the common multiple, or a sum of 1 and the common multiple of the n.

Note that it may be difficult to describe the process in which an unused measuring unit is supplied to the turntable to be supported thereon as a "process . . . performed on the measuring units situated at different positions on the turntable", because the measuring unit is situated on the turntable after this process is complete. However, in this specification, the measurement unit supply process is included as this type of process.

In addition, the k types of processes need not be performed on all of the measuring units situated at different positions on the turntable every time that the turntable is stopped. For example, when measurement is initiated, the first process is to supply a measuring unit to the turntable. Because there are no other measuring units on the turntable at this time, the other processes, such as supplying a sample to a measuring unit, irradiating of the light beam, and the detecting of the intensity are not performed.

The measuring apparatus of the present invention is equipped with the turntable and the drive means. The turntable is used for supporting n measuring units at intervals of a predetermined angle with respect to a rotation axis thereof. The drive means is used for rotating the turntable intermittently at intervals of an angle equal to m times the predetermined angle (m is an integer). When the turntable is stopped, k kinds of processes are respectively performed on the measuring units situated at different positions on the turntable. The above-mentioned k is 2≦k≦n, and the above-mentioned m is either 1, a number that is neither the common divisor of n nor the common multiple, or a sum of 1 and the common multiple of n.

With this arrangement, the n measuring units on the turntable can be fed in regular sequence, while avoiding the case in which before one measuring unit is fed once to sections in which the k kinds of processes are performed, another measuring unit is fed many times. That is, if the turntable is stopped n times, each of the n measuring units on the turntable is fed once to each processing section. Thus, the measuring apparatus of the present invention is capable of efficiently performing the above-mentioned k kinds of processes on each measuring unit.

The measuring apparatus, utilizing ATR, of the present invention is likewise able to obtain the same effect as the aforementioned effect.

BRIEF DESCRIPTION OF THE DRAWINGS

The present invention will be described in further detail with reference to the accompanying drawings wherein.

DESCRIPTION OF THE PREFERRED EMBODIMENTS

Figure 1:
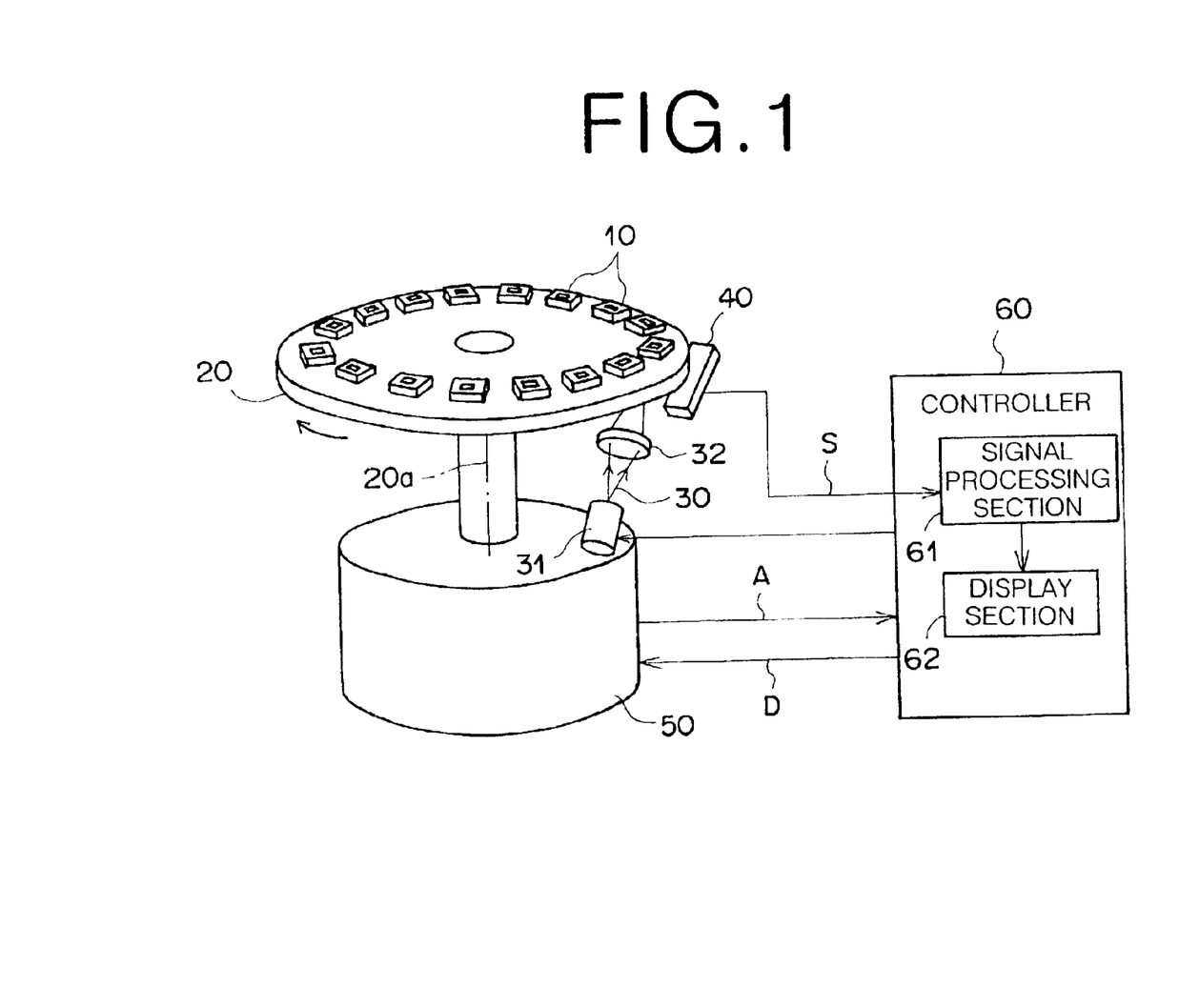
FIG. 1 is a perspective view showing a surface plasmon resonance measuring apparatus constructed according to a first embodiment of the present invention.
Figure 2:
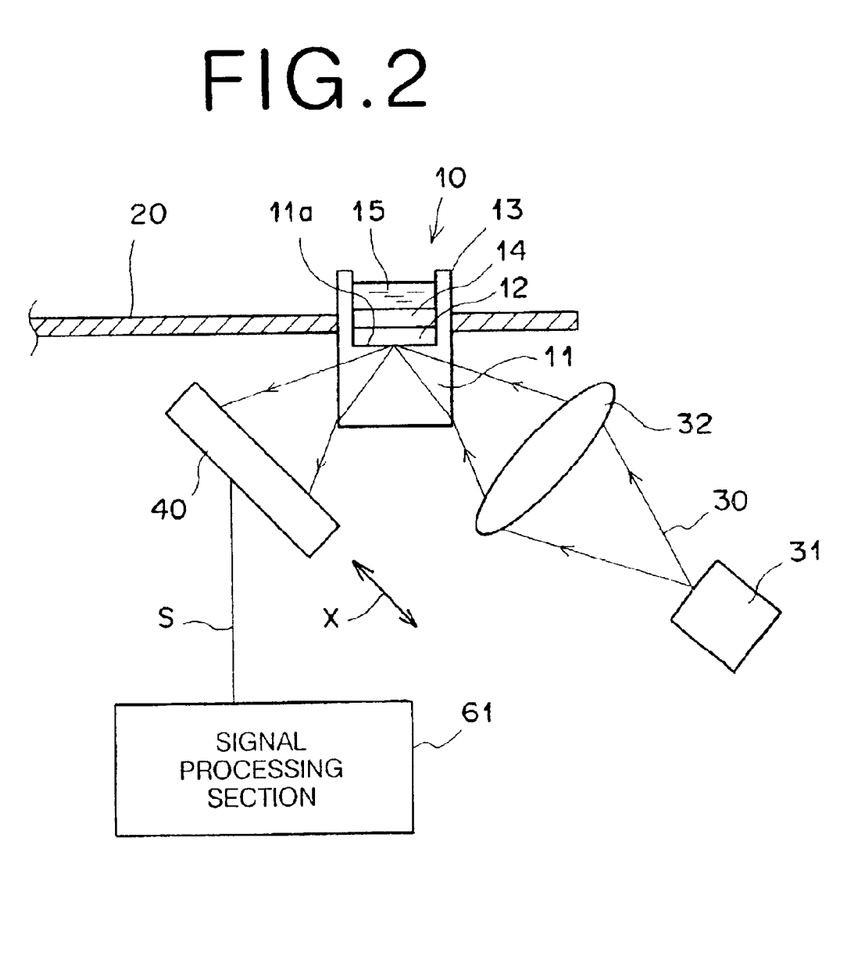
FIG. 2 is a partial-sectional side view showing the essential parts of the surface plasmon resonance measuring apparatus of FIG. 1.
Figure 3:
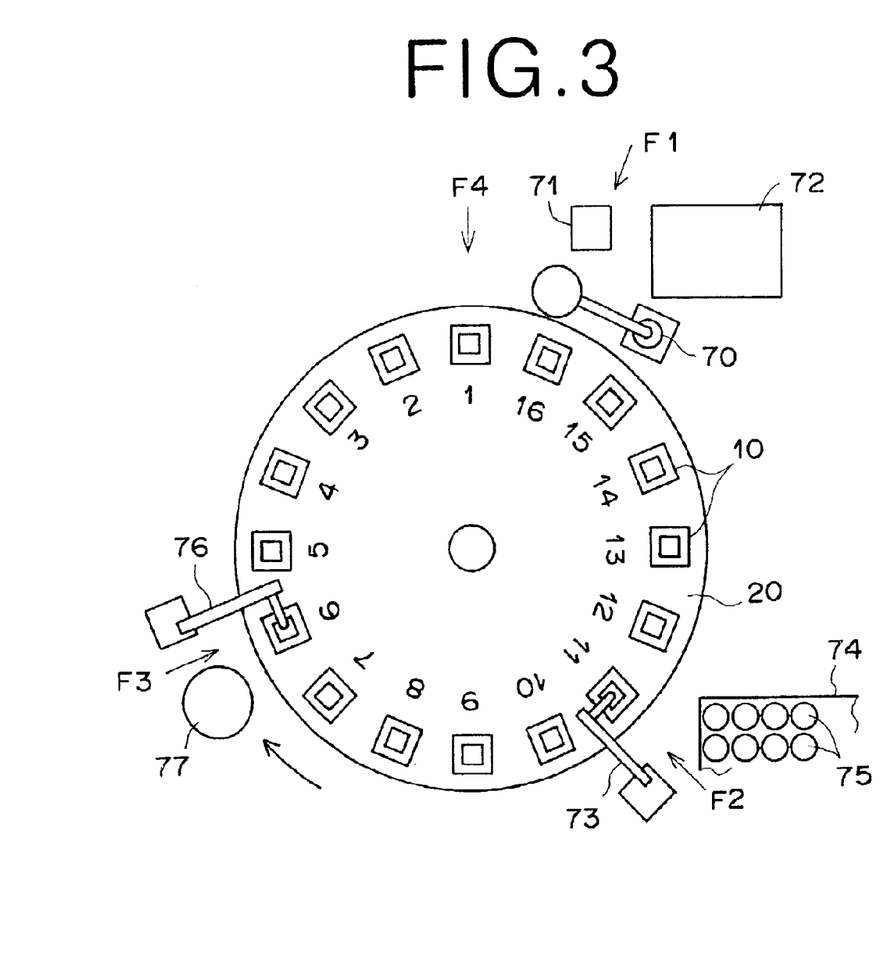
FIG. 3 is a plan view showing the essential parts of the surface plasmon resonance measuring apparatus of FIG. 1.

Referring now in greater detail to the drawings and initially to FIGS. 1 to 3, there is shown a surface plasmon resonance measuring apparatus in accordance with a first embodiment of the present invention.

As shown in FIG. 1, the surface plasmon resonance measuring apparatus has a plurality of measuring units 10, a turntable 20 for supporting the measuring units 10, and a laser light source (e.g., a semiconductor laser) 31 for emitting a measuring light beam (e.g., a laser beam) 30. The measuring apparatus further has a condenser lens 32 constituting an optical incidence system, a photodetector 40, supporting-body drive means 50 for rotating the above-mentioned turntable 20 intermittently, and a controller 60. The controller 60 is used for controlling the supporting-body drive means 50 and also for receiving an output signal S from the photodetector 40 and performing a process that is to be described later.

The measuring unit 10, as shown in FIG. 2, is constructed of a transparent dielectric block 11, a metal film 12, and a sample holding frame 13. The transparent dielectric block 11 is formed, for example, into the shape of a rectangular parallelepiped. The metal film 12 is formed on the top surface of the dielectric block 11 and made, for example, of silver, copper, aluminum, etc. The sample holding frame 13 consists of a cylindrical member, which is formed on the dielectric block 11 so that the metal film 12 is exposed to the outside. The sample holding frame 13 holds, for example, a liquid sample 15, as described later.

The dielectric block 11 and the sample holding frame 13 constitute the measuring unit 10 and are integrally formed, for example, from transparent resin, etc. The measuring unit 10 constitutes a measuring chip exchangeable with respect to the turntable 20. For example, the measuring unit 10 can be detachably fitted in a through hole formed in the turntable 20 in order to make it exchangeable. In the first embodiment, a sensing medium 14, which is to be described later, is fixed on the metal film 12.

The turntable 20 is constructed so that a plurality of measuring units 10 are supported at equiangular intervals (e.g., intervals of 22.5 degrees) on a circle with respect to the rotation axis 20a thereof. In the first embodiment, sixteen measuring units 10 are supported. The supporting-body drive means 50 is constructed of a stepping motor, etc., and is rotated intermittently at intervals of an angle equal to five times the pitch between the measuring units 10, that is, at intervals of 112.5 degrees. That is, in the first embodiment, the aforementioned value of m is 5.

The condenser lens 32, as shown in FIG. 2, collects the light beam 30 and makes the light beam 30 enter the dielectric body 11 so that the light beam 30 converges on an interface 11a between the dielectric block 11 and the metal film 12. Thus, the light beam 30 enters the dielectric block 11 so that it includes components incident on the interface 11a at various angles of incidence. The incidence angle range includes an angle range in which a total internal reflection condition for the light beam 30 is satisfied at the interface 11a, and in which surface plasmon resonance can occur.

Note that the light beam 30 is made to strike the interface 10b as a p-polarized light beam. For this reason, it is necessary to dispose the laser light source 31 so that the polarization direction thereof becomes a predetermined direction. In addition, the polarization direction of the light beam 30 may be controlled with a wavelength plate, a polarizing plate, etc.

The photodetector 40 is used for detecting the intensity of the light beam 30 totally reflected at the interface 11a. This photodetector 40 is constructed of a line sensor having a large number of light-receiving elements arranged in a row. The light-receiving elements are arranged along the direction of arrow X in FIG. 2.

On the other hand, the controller 60 receives an address signal A, representing a position where rotation of the supporting-body drive means 50 is stopped, from the supporting-body drive means 50. This controller 60 also outputs a drive signal D to operate the supporting-body drive means 50, based on a predetermined sequence. The controller 60 is equipped with a signal processing section 60 for receiving the aforementioned output signal S from the photodetector 40, and a display section 62 for receiving an output signal from the signal processing section 61.

As shown in FIG. 3, the surface plasmon resonance measuring apparatus of the first embodiment is provided with four processing stations, a measuring-unit supply station F1, a sample pouring station F2, an oil pouring station F3, and a photometer station F4, along the circumference of the turntable 20 by which the measuring units 10 are supported. Processes to be described later are performed at the stations, respectively. Thus, in the first embodiment, the aforementioned value of k is 4.

At the measuring-unit supply station F1, measuring units 10 are supplied to the turntable 20 by chip supply means 70, and after the measurements, the measuring units 10 are removed from the turntable 20. This chip supply means 70 is constructed of an air suction cap well known in the prior art and a drive mechanism therefor. The chip supply means 70 takes out measuring units 10 one by one from a cassette 71 and supplies them to the turntable 20. The chip supply means 70 holds the measuring unit 10, supported in the turntable 20, by suction and removes it from the turntable 20, and drops the measuring unit 10 into a discharge tray 72.

At the sample pouring station F2, a liquid sample stored in a well 75 in a sample tray 74 is poured into the sample holding frame (see FIG. 2) of the measuring unit 10 by a sample pouring device 73. The sample pouring device 73 is constructed of a pipette, connected to a negative pressure source, for holding a liquid sample by suction, means for moving the pipette, etc.

At the oil pouring station F3, oil stored in an oil container 77 is poured by an oil pouring device 76 similar to the sample pouring device 73 into the sample holding frame 13 of the measuring unit 10 to which the liquid sample has already been supplied at the sample pouring station F2. This oil is poured in order to prevent the sample stored in the sample holding frame 13 of the measuring unit from evaporating.

At the photometer station F4, the state of ATR due to surface plasmon resonance to be described later is detected by the aforementioned laser light source 31, condenser lens 32, and photodetector 40. Note that since the laser light source 31, condenser lens 32, and photodetector 40 are disposed behind the turntable 20 shown in FIG. 3, they are not shown in FIG. 3.

A description will hereinafter be given of how a sample is analyzed by the surface plasmon resonance measuring apparatus constructed as described above. The turntable 21 is first rotated intermittently at intervals of an angle equal to five times the pitch between the measuring units 10 by the supporting-body drive means 50, as mentioned above. When the turntable 20 is stopped, supply or removal of a measuring unit 10 is performed at the measuring-unit supply station F1. In addition, a liquid sample is supplied to the measuring unit 10 stopped at the sample pouring station F2, oil is supplied to the measuring unit 10 stopped at the sample pouring station F3, and a surface plasmon resonance measurement is performed on the measuring unit 10 stopped at the photometer station F4.

Now, the surface plasmon resonance measurement that is made at the photometer station F4 will be described with reference to FIG. 2. At the photometer station F4, the measuring unit 10 with a sample held in the sample holding frame 13 is stopped at the position where the aforementioned light beam 30 enters the dielectric body 11. At this stage, the laser light source 31 is driven in response to an output signal from the controller 60. Then, the light beam 30 emitted from the laser light source 31 is collected and directed to the dielectric block 11 by the condenser lens 32 and strikes the interface 11a between the dielectric block 11 and the metal film 12. The light beam 30 totally reflected at the interface 11a is detected by the photodetector 40.

Since the light beam 30 is collected and directed to the dielectric block 11 and converges at the interface 11a, as described above, the light beam 30 includes components incident on the interface 11a at various incidence angles θ. Note that these incidence angles θ are greater than a critical angle at which total internal reflection occurs. Hence, the light beam 30 is totally reflected at the interface 11a, and the reflected light beam includes components reflected at various angles.

When the light beam 30 is totally reflected as described above, an evanescent wave propagates on the side of the metal film 12 through the interface 11a. And when the light beam 30 strikes the interface 11a at a specific incidence angle $\theta_{sp}$, the evanescent wave resonates with the surface plasmon excited at the surface of the metal film 12. Because of this, the intensity I of the light reflected at the interface 11a drops sharply. The relationship between the specific incidence angle $\theta_{sp}$ and the intensity I is schematically shown in FIG. 4.

The quantity of light detected by each light-receiving element is calculated from the light-quantity detection signal S output from the photodetector 40. Based on the position of the light-receiving element that detected a dark line, the specific incidence angle $\theta_{sp}$ (at which ATR occurs) is calculated. And based on a curve for the relationship between the intensity I and the incidence angle $\theta_{sp}$, a specific substance in the sample 15 can be quantitatively analyzed. The signal processing section 61 of the controller 60 quantitatively analyzes a specific substance in the sample 15, based on the principle described above. The result of analysis is displayed on the display section 62.

Note that the sensing substance 14 fixed on the surface of the metal film 12 bonds with a specific substance in the sample 15. As combination of the specific substance and the sensing substance 14, there is combination of an antigen and antibody. In that case, an antigen-antibody reaction can be detected based on the aforementioned specific incidence angle $\theta_{sp}$ (at which ATR occurs).

Figure 4:
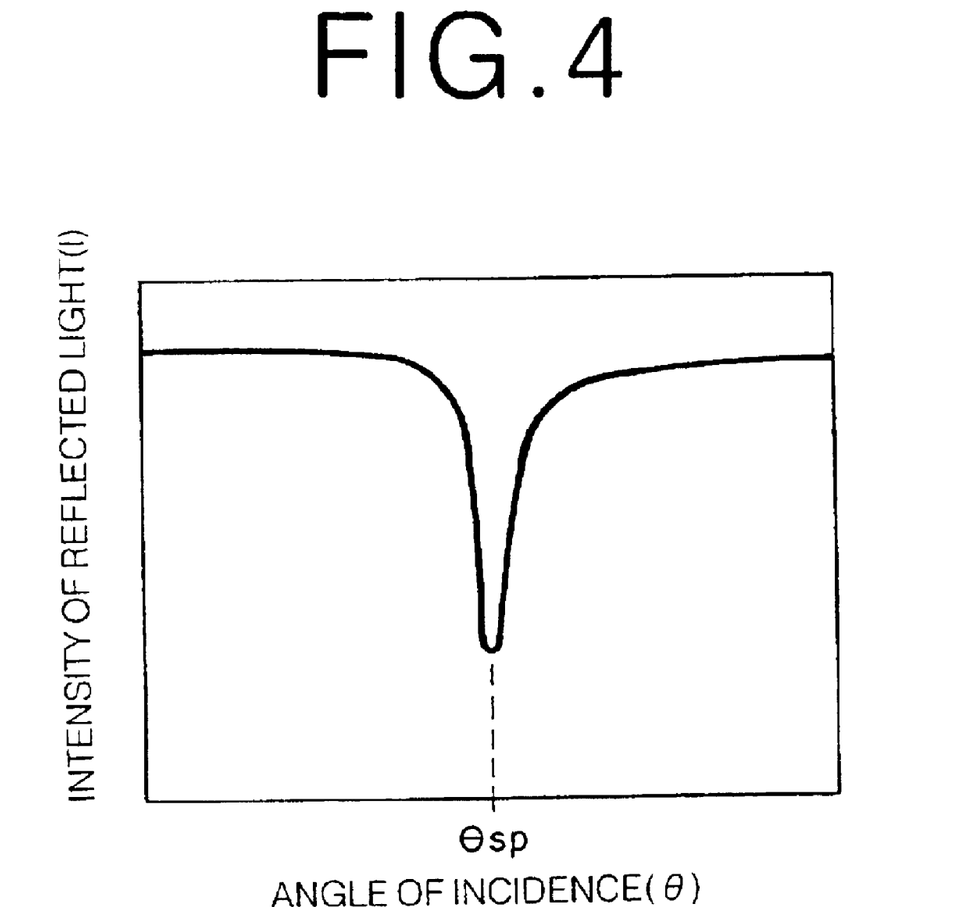
FIG. 4 is a graph showing the relationship between the incidence angle at which a light beam enters the measuring unit of the measuring apparatus, and the intensity of the light beam reflected at the measuring unit.

That is, the refractive index of the sensing substance 14 changes according to the bond state between the specific substance and the sensing substance 14, and the specific incidence angle $\theta_{sp}$ represented by the characteristic curve of FIG. 4 is horizontally moved. Therefore, an antigen-antibody reaction can be detected according to the specific incidence angle $\theta_{sp}$. In this case, both the sample 15 and the sensing substance are samples to be analyzed.

In the surface plasmon resonance measuring apparatus, as described above, a plurality of measuring units 10 are supported by the turntable 20 and are serially located at the photometer station F4 by moving the turntable 20. Therefore, the samples 15 held in the sample holding frames 13 of the measuring units 10 can be measured serially by movement of the turntable 20. Thus, the surface plasmon resonance measuring apparatus of the first embodiment is capable of measuring a large number of samples 15 in a short time.

Next, with reference to FIG. 3, a detailed description will be given of how the measuring unit 10 is fed to the measuring-unit supply station F1, sample pouring station F2, oil pouring station F3, and photometer station F4. The portions of the turntable 20 that support the measuring units 10 are referred to as channels. The channels are numbered from 1 to 16, as shown in FIG. 3.

Suppose that at the first stage of the measuring operation, the turntable 20 is stopped as shown in FIG. 3. That is, channel 16 is situated at the measuring-unit supply station F1, channel 11 at the sample pouring station F2, channel 6 at the oil pouring station F3, and channel 1 at the photometer station F4. At the first stage, only a measuring unit 10 supply operation is performed at the measuring-unit supply station F1.

The turntable 20 is rotated through a predetermined angle (five times the pitch between the measuring units 10) from this state in the clockwise direction and is stopped. In the stopped state of the turntable 20 at the second stage, channel 5 is situated at the measuring-unit supply station F1, channel 16 at the sample pouring station F2, channel 11 at the oil pouring station F3, and channel 6 at the photometer station F4. At the second stage, a measuring unit 10 is supplied at the measuring-unit supply station F1, and a sample is poured at the sample pouring station F2.

The turntable 20 is rotated through the predetermined angle from this state and is stopped. In the stopped state of the turntable 20 at the third stage, channel 10 is situated at the measuring-unit supply station F1, channel 5 at the sample pouring station F2, channel 16 at the oil pouring station F3, and channel 11 at the photometer station F4. At the third stage, a measuring unit 10 is supplied at the measuring-unit supply station F1, a sample is poured at the sample pouring station F2, and oil is poured at the oil pouring station F3.

The turntable 20 is rotated through the predetermined angle from this state and is stopped. In the stopped state of the turntable 20 at the fourth stage, channel 15 is situated at the measuring-unit supply station F1, channel 10 at the sample pouring station F2, channel 5 at the oil pouring station F3, and channel 16 at the photometer station F4. At the fourth stage, a measuring unit 10 is supplied at the measuring-unit supply station F1, a sample is poured at the sample pouring station F2, oil is poured at the oil pouring station F3, and surface plasmon resonance is measured at the photometer station F4.

Thereafter, the turntable 20 is similarly rotated the predetermined angle at a time, and the processes at the stations F1, F2, F3, and F4 are simultaneously performed. At each stage, channels that are processed at each station are listed in Tables 1, 2, and 3. In these tables, channels enclosed within a frame are not processed even if they are passed through a station. Among the channels, the "○ channel" indicates that there is no measuring unit in the ○ channel, In addition, in the process which is performed at the measuring-unit supply station F1, the "channel S," "channel R," and "channel RS" indicate the process of supplying a new measuring unit 10 to the channel S, the process of removing the measuring unit 10 held at the channel R, and the process of removing the measuring unit 10 held at the channel RS and then supplying a new measuring unit 10 to the channel RS, respectively.

TABLE 1

| Stages | Unit supply station F1 | Sample pouring station F2 | Oil pouring station F3 | Photometer station F4 |
|---|---|---|---|---|
| 1 | channel 16 S | channel 11 | channel 6 | channel 1 |
| 2 | channel 5 S | channel 16 | channel 11 | channel 6 |
| 3 | channel 10 S | channel 5 | channel 16 | channel 11 |
| 4 | channel 15 S | channel 10 | channel 5 | channel 16 |
| 5 | channel 4 S | channel 15 | channel 10 | channel 5 |
| 6 | channel 9 S | channel 4 | channel 15 | channel 10 |
| 7 | channel 14 S | channel 9 | channel 4 | channel 15 |
| 8 | channel 3 S | channel 14 | channel 9 | channel 4 |
| 9 | channel 8 S | channel 3 | channel 14 | channel 9 |
| 10 | channel 13 S | channel 8 | channel 3 | channel 14 |
| 11 | channel 2 S | channel 13 | channel 8 | channel 3 |
| 12 | channel 7 S | channel 2 | channel 13 | channel 8 |
| 13 | channel 12 S | channel 7 | channel 2 | channel 13 |
| 14 | channel 1 S | channel 12 | channel 7 | channel 2 |
| 15 | channel 6 S | channel 1 | channel 12 | channel 7 |
| 16 | channel 11 S | channel 6 | channel 1 | channel 12 |

TABLE 1-continued

| Stages | Unit supply station F1 | Sample pouring station F2 | Oil pouring station F3 | Photometer station F4 |
|---|---|---|---|---|
| 17 | channel 16 | channel 11 | channel 6 | channel 1 |
| 18 | channel 5 | channel 16 | channel 11 | channel 6 |
| 19 | channel 10 | channel 5 | channel 16 | channel 11 |
| 20 | channel 15 | channel 10 | channel 5 | channel 16 |
| 21 | channel 4 | channel 15 | channel 10 | channel 5 |
| 22 | channel 9 | channel 4 | channel 15 | channel 10 |
| 23 | channel 14 | channel 9 | channel 4 | channel 15 |
| 24 | channel 3 | channel 14 | channel 9 | channel 4 |
| 25 | channel 8 | channel 3 | channel 14 | channel 9 |
| 26 | channel 13 | channel 8 | channel 3 | channel 14 |
| 27 | channel 2 | channel 13 | channel 8 | channel 3 |
| 28 | channel 7 | channel 2 | channel 13 | channel 8 |
| 29 | channel 12 | channel 7 | channel 2 | channel 13 |
| 30 | channel 1 | channel 12 | channel 7 | channel 2 |
| 31 | channel 6 | channel 1 | channel 12 | channel 7 |
| 32 | channel 11 | channel 6 | channel 1 | channel 12 |

TABLE 2

| Stages | Unit supply station F1 | Sample pouring station F2 | Oil pouring station F3 | Photometer station F4 |
|---|---|---|---|---|
| 33 | channel 16 | channel 11 | channel 6 | channel 1 |
| 34 | channel 5 | channel 16 | channel 11 | channel 6 |
| 35 | channel 10 | channel 5 | channel 16 | channel 11 |
| 36 | channel 15 | channel 10 | channel 5 | channel 16 |
| 37 | channel 4 | channel 15 | channel 10 | channel 5 |
| 38 | channel 9 | channel 4 | channel 15 | channel 10 |
| 39 | channel 14 | channel 9 | channel 4 | channel 15 |
| 40 | channel 3 | channel 14 | channel 9 | channel 4 |
| 41 | channel 8 | channel 3 | channel 14 | channel 9 |
| 42 | channel 13 | channel 8 | channel 3 | channel 14 |
| 43 | channel 2 | channel 13 | channel 8 | channel 3 |
| 44 | channel 7 | channel 2 | channel 13 | channel 8 |
| 45 | channel 12 | channel 7 | channel 2 | channel 13 |
| 46 | channel 1 | channel 12 | channel 7 | channel 2 |
| 47 | channel 6 | channel 1 | channel 12 | channel 7 |
| 48 | channel 11 | channel 6 | channel 1 | channel 12 |
| 49 | channel 16 RS | channel 11 | channel 6 | channel 1 |
| 50 | channel 5 RS | channel 16 | channel 11 | channel 6 |
| 51 | channel 10 RS | channel 5 | channel 16 | channel 11 |
| 52 | channel 15 RS | channel 10 | channel 5 | channel 16 |
| 53 | channel 4 RS | channel 15 | channel 10 | channel 5 |
| 54 | channel 9 RS | channel 4 | channel 15 | channel 10 |
| 55 | channel 14 RS | channel 9 | channel 4 | channel 15 |
| 56 | channel 3 RS | channel 14 | channel 9 | channel 4 |
| 57 | channel 8 RS | channel 3 | channel 14 | channel 9 |
| 58 | channel 13 RS | channel 8 | channel 3 | channel 14 |
| 59 | channel 2 RS | channel 13 | channel 8 | channel 3 |
| 60 | channel 7 RS | channel 2 | channel 13 | channel 8 |
| 61 | channel 12 RS | channel 7 | channel 2 | channel 13 |
| 62 | channel 1 RS | channel 12 | channel 7 | channel 2 |
| 63 | channel 6 RS | channel 1 | channel 12 | channel 7 |
| 64 | channel 11 RS | channel 6 | channel 1 | channel 12 |
| . | . | . | . | . |
| . | . | . | . | . |
| . | . | . | . | . |

TABLE 3

| Stages | Unit supply station F1 | Sample pouring station F2 | Oil pouring station F3 | Photometer station F4 |
|---|---|---|---|---|
| 16j–17 | channel 6 | channel 1 | channel 12 | channel 7 |
| 16j–16 | channel 11 | channel 6 | channel 1 | channel 12 |
| 16j–15 | channel 16 R | channel 11 | channel 6 | channel 1 |
| 16j–14 | channel 5 R ○ | channel 16 | channel 11 | channel 6 |
| 16j–13 | channel 10 R ○ | channel 5 ○ | channel 16 | channel 11 |
| 16j–12 | channel 15 R ○ | channel 10 ○ | channel 5 ○ | channel 16 |
| 16j–11 | channel 4 R ○ | channel 15 ○ | channel 10 ○ | channel 5 |
| 16j–10 | channel 9 R ○ | channel 4 ○ | channel 15 ○ | channel 10 |

TABLE 3-continued

| Stages | Unit supply station F1 | Sample pouring station F2 | Oil pouring station F3 | Photo-meter station F4 |
|---|---|---|---|---|
| 16j–9 | channel 14 R ○ | channel 9 ○ | channel 4 ○ | channel 15 |
| 16j–8 | channel 3 R ○ | channel 14 ○ | channel 9 ○ | channel 4 |
| 16j–7 | channel 8 R ○ | channel 3 ○ | channel 14 ○ | channel 9 |
| 16j–6 | channel 13 R ○ | channel 8 ○ | channel 3 ○ | channel 14 |
| 16j–5 | channel 2 R ○ | channel 13 ○ | channel 8 ○ | channel 3 |
| 16j–4 | channel 7 R ○ | channel 2 ○ | channel 13 ○ | channel 8 |
| lGj–3 | channel 12 R ○ | channel 7 ○ | channel 2 ○ | channel 13 |
| 16j–2 | channel 1 R ○ | channel 12 ○ | channel 7 ○ | channel 2 |
| 16j–1 | channel 6 R ○ | channel 1 ○ | channel 12 ○ | channel 7 |
| 16j | channel 11 R ○ | channel 6 ○ | channel 1 ○ | channel 12 |
| . | . | . | . | . |
| . | . | . | . | . |

In the first embodiment, as described previously, the number of the measuring units 10 supported by the turntable 20 is n=16 and the turntable 20 is rotated intermittently at intervals of an angle equal to five times the pitch between the measuring units 10 (m=5). In addition, when the turntable 20 is stopped, the measuring units 10 held at four positions (k=4) are processed. That is, four processes are performed in total (however, there are cases where depending on the stage, some of the four processes are not performed).

In the first embodiment, as evident in Tables 1, 2, and 3, surface plasmon resonance is measured three times for the sample 15 of a single measuring unit 10. The measuring unit 10 for which the three measurements was made is removed from the turntable 20, and a new measuring unit 10 is supplied to the turntable 20 (e.g., see stages 49 to 64 in Table 2). The measurement of surface plasmon resonance is also made three times for the new measuring unit 10. Finally, as shown in the stages 16j–15 to 16j of Table 3, the process of removing the measuring unit 10 from the turntable 20 is carried out and the sequence of processes is completed.

In the case of the above-mentioned n=16, m=5, and k=4, the aforementioned relation of 2≦n is satisfied. Meanwhile, m=5 is neither the common divisor of n=16 nor the common multiple. In the first embodiment with n=16, m=5, and k=4, as evident in Table 1, the 16 measuring units on the turntable 20 are fed in regular sequence, while avoiding the case in which before one measuring unit 10 is fed once to the stations F1, F2, F3, and F4 in which four processes are performed, another measuring unit 10 is fed many times. Hence, the measuring apparatus of the first embodiment is capable of efficiently performing the above-mentioned 4 processes on each measuring unit 10. Of course, combination of n, m, and k is not to be limited to n=16, m=5, and k=4. If the numbers of n, m, and k are set as predefined in the present invention, the above-mentioned effects are similarly obtainable. For instance, as an extremely simple example, m=1 can be set.

Figure 5:
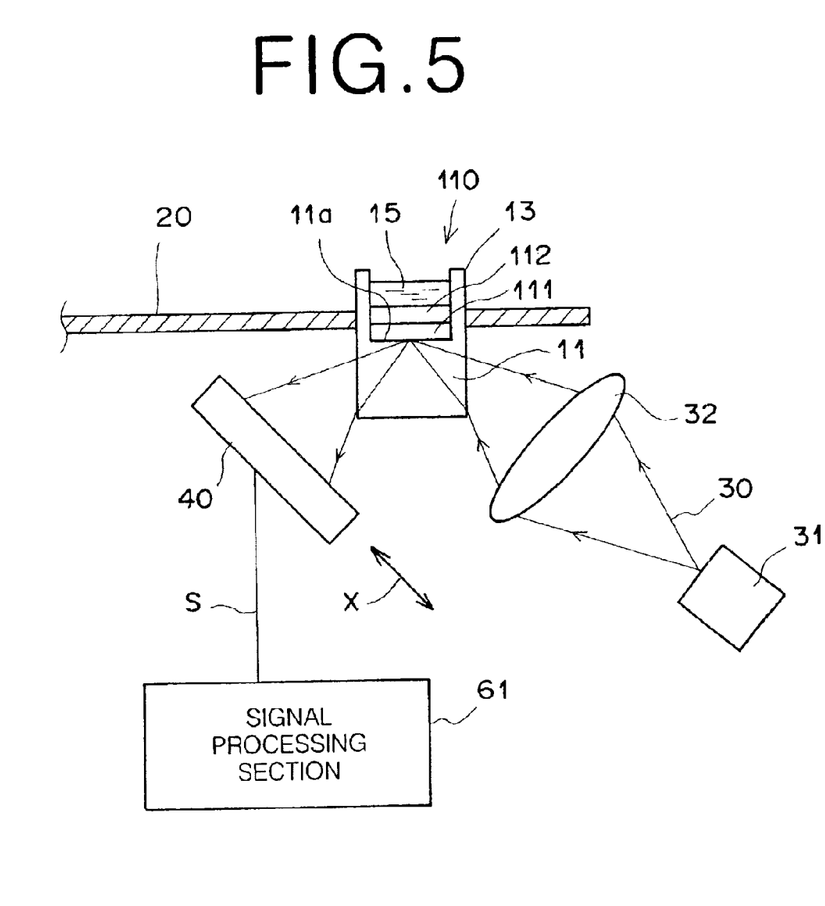
FIG. 5 is a partial-sectional side view showing a leaky mode resonance measuring apparatus constructed according to a second embodiment of the present invention.

FIG. 5 shows a measuring apparatus (leaky mode measuring apparatus) utilizes ATR, constructed according to a second embodiment of the present invention. Note in the figure that the same reference numerals are applied to the same parts as those in FIG. 2, and that a description thereof will not be given unless particularly necessary (the same applies to the following descriptions).

The leaky mode measuring apparatus of the second embodiment also employs a measuring unit (measuring chip) 110. The top surface of a dielectric block 11 constituting the measuring unit 110 has a cladding layer 111 on which an optical waveguide layer 112 is formed.

The dielectric block 11 is formed, for example, from synthetic resin, or optical glass such as BK7, etc. The cladding layer 111 is formed into the shape of a thin film by employing a dielectric lower in refractive index than the dielectric block 11, or metal such as gold, etc. The optical waveguide layer 112 is also formed into a thin film by employing a dielectric, such as such as polymethyl-methacrylate (PMMA), higher in refractive index than the cladding layer 111. The cladding layer 111 is, for example, 36.5 nm in thickness when it is formed from a thin gold film. The optical waveguide layer 112 is, for example, about 700 nm in thickness when it is formed from PMMA.

In the leaky mode measuring apparatus of the second embodiment, the measuring unit 110 differs in construction from the measuring unit 10, but the points other than that, including the aforementioned values for n, m, and k, are basically the same as the first embodiment.

In the leaky mode measuring apparatus of the second embodiment, if a light beam 30 emitted from a laser light source 31 strikes the cladding layer 111 through the dielectric block 11 at incidence angles greater than an angle at which total internal reflection (TIR) occurs, the light beam 30 is totally reflected at the interface 11a between the dielectric block 11 and the cladding layer 111. However, the light with a specific wave number, incident on the optical waveguide layer 112 through the cladding layer 111 at a specific incidence angle, propagates through the optical waveguide layer 112 in a waveguide mode. If the waveguide mode is excited in this manner, the greater part of the incident light is confined within the optical waveguide layer 112, and consequently, ATR occurs in which the intensity of the light totally reflected at the interface 11a drops sharply.

The wave number of the light in the optical waveguide layer 112 depends on the refractive index of a sample 15 on the optical waveguide layer 112. Therefore, the refractive index of the sample 15 and the properties of the sample related to the refractive index can be analyzed by finding the above-mentioned specific incidence angle $\theta_{sp}$ at which ATR takes place. A signal processing section 61 is used for quantitatively analyzing a specific substance in the sample 15, based on the aforementioned principle. The result of analysis is displayed on a display section (not shown).

Since the leaky mode measuring apparatus of the second embodiment similarly has values of 16, 5, and 4 for aforementioned n, m, and k, the same effects as those obtained in the first embodiment can be obtained.

Figure 6:
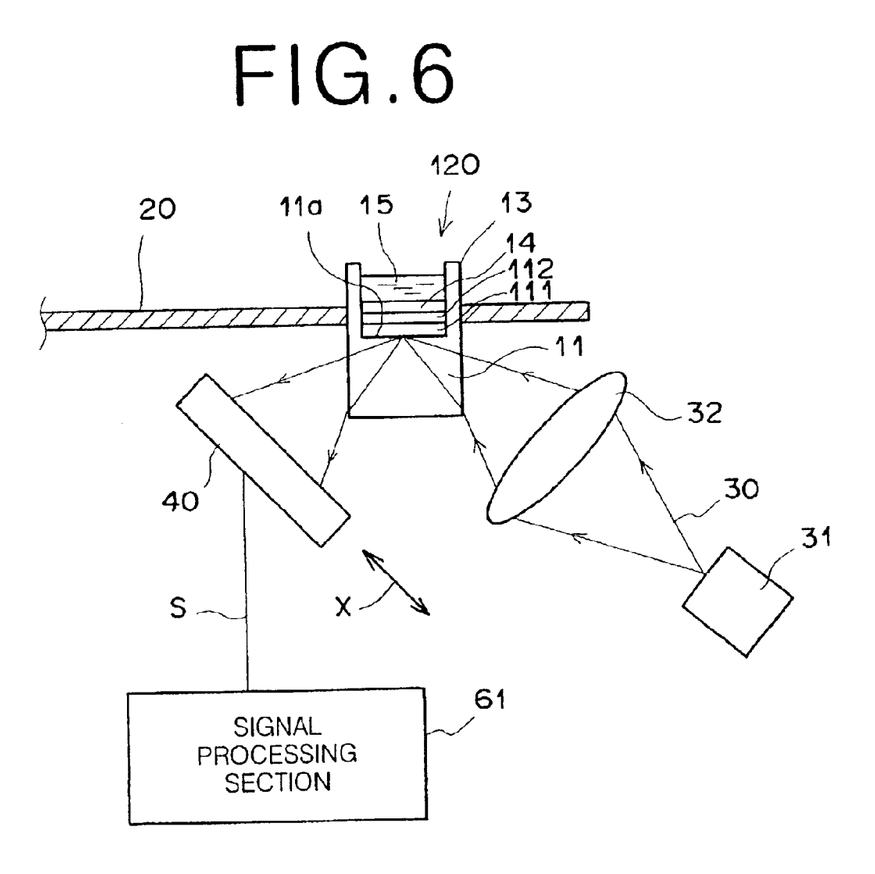
FIG. 6 is a partial-sectional side view showing a leaky mode resonance measuring apparatus constructed according to a third embodiment of the present invention.

FIG. 6 shows a measuring apparatus (leaky mode measuring apparatus) utilizes ATR, constructed according to a third embodiment of the present invention. The leaky mode measuring apparatus of the third embodiment likewise employs a measuring unit (measuring chip) 120. The top surface of a dielectric block 11 constituting the measuring unit 120 has a cladding layer 111 on which an optical waveguide layer 112 is formed. The optical waveguide layer 112 has a sensing substance 14 fixed thereon.

The measuring apparatus of the third embodiment differs from the apparatus of FIG. 5 only in that in the measuring unit 120 the sensing substance 14 is fixed.

The sensing substance 14, as with the sensing substance 14 in the measuring apparatus of FIG. 2, bonds with a specific substance in the sample 15. As with the first embodiment, combination of an antigen and an antibody is taken as an example of the combination of the specific substance and the sensing substance 14.

As in the first embodiment, the relationship between the incidence angle θ and light intensity I of the light beam 30 relative to the interface 11a is basically the same as that shown in FIG. 4. That is, the refractive index of the sensing substance 14 changes according to the bond between the specific substance and the sensing substance 14, and the effective refractive index of the optical waveguide layer 112 changes. Therefore, since the above-mentioned relationship changes, an antigen-antibody reaction can be detected based on the specific incidence angle $\theta_{sp}$ at which ATR occurs.

The third embodiment likewise has the same effect as that obtained in the first embodiment or second embodiment, because it has values of 16, 5, and 4 for aforementioned n, m, and k.

While the measuring apparatuses utilizing ATR have been described, the present invention is not to be limited to them. The invention is generally applicable to a measuring apparatus in which a plurality of measuring units are supported by a turntable, and in which various processes are performed on the measuring unit each time the turntable is stopped. The measuring apparatus can likewise have the same effects as those obtained in the aforementioned embodiments.

Finally, although the present invention has been described with reference to the preferred embodiments thereof, the invention is not to be limited to the details given herein, but may be modified within the scope of the invention hereinafter claimed.

What is claimed is:

1. A measuring apparatus utilizing attenuated total reflection, comprising:
    n measuring units comprising
        a dielectric block, a thin film layer formed on one surface of said dielectric block, and a sample holding mechanism for holding a sample on said thin film layer;
    a turntable for supporting said n measuring units at intervals of a predetermined angle with respect to a rotation axis thereof;
    drive means for rotating said turntable intermittently at intervals of an angle equal to m times said predetermined angle (m is an integer);
    a light source for emitting a light beam;
    an optical system for making said light beam enter said dielectric block of said measuring unit, situated at a predetermined position when said turntable is stopped, at various angles of incidence so that a condition for total internal reflection is satisfied at an interface between said dielectric block and said thin film; and
    photodetection means for measuring intensity of said light beam totally reflected at said interface to detect said attenuated total reflection;
    wherein, when said turntable is stopped, k kinds of processes, including irradiation of said light beam and the detection of the intensity, are respectively performed on said measuring units situated at different positions on said turntable;
    and wherein said k is $2 \leq k \leq n$ and said m is either 1, a number that is neither the common divisor of 1 and said n nor the common multiple, or a sum of 1 and the common multiple of said n.

2. A measuring apparatus utilizing attenuated total reflection, comprising:
    n measuring units comprising
        a dielectric block, a thin film layer, which comprises a metal film, formed on one surface of said dielectric block, and a sample holding mechanism for holding a sample on said thin film layer;
    a turntable for supporting said n measuring units at intervals of a predetermined angle with respect to a rotation axis thereof;
    drive means for rotating said turntable intermittently at intervals of an angle equal to m times said predetermined angle (m is an integer);
    a light source for emitting a light beam;
    an optical system for making said light beam enter said dielectric block of said measuring unit, situated at a predetermined position when said turntable is stopped, at various angles of incidence so that a condition for total internal reflection is satisfied at an interface between said dielectric block and said metal film; and
    photodetection means for measuring intensity of said light beam totally reflected at said interface to detect said attenuated total reflection due to surface plasmon resonance;
    wherein, when said turntable is stopped, k kinds of processes, including irradiation of said light beam and the detection of the intensity, are respectively performed on said measuring units situated at different positions on said turntable;
    and wherein said k is $2 \leq k \leq n$ and said m is either 1, a number that is neither the common divisor of 1 and said n nor the common multiple, or a sum of 1 and the common multiple of said n.

3. A measuring apparatus utilizing attenuated total reflection, comprising:
    n measuring units comprising
        a dielectric block, a thin film layer, which comprises a cladding layer and an optical waveguide layer formed on said cladding layer, formed on one surface of said dielectric block, and a sample holding mechanism for holding a sample on said thin film layer;
    a turntable for supporting said n measuring units at intervals of a predetermined angle with respect to a rotation axis thereof;
    drive means for rotating said turntable intermittently at intervals of an angle equal to m times said predetermined angle (m is an integer);
    a light source for emitting a light beam;
    an optical system for making said light beam enter said dielectric block of said measuring unit, situated at a predetermined position when said turntable is stopped, at various angles of incidence so that a condition for total internal reflection is satisfied at an interface between said dielectric block and said cladding layer; and
    photodetection means for measuring intensity of said light beam totally reflected at said interface to detect said attenuated total reflection due to a waveguide mode excited at said optical waveguide layer;
    wherein, when said turntable is stopped, k kinds of processes, including irradiation of said light beam and the detection of the intensity, are respectively performed on said measuring units situated at different positions on said turntable;
    and wherein said k is $2 \leq k \leq n$ and said m is either 1, a number that is neither the common divisor of 1 and said n nor the common multiple, or a sum of 1 and the common multiple of said n.

* * * * *